(12) United States Patent
Rudko et al.

(10) Patent No.: US 7,537,592 B2
(45) Date of Patent: May 26, 2009

(54) ENDOVASCULAR TISSUE REMOVAL DEVICE

(75) Inventors: Robert I Rudko, Holliston, MA (US);
Mark R. Tauscher, Medfield, MA (US);
Richard P. Yeomans, Jr., Medway, MA (US)

(73) Assignee: PLC Medical Systems, Inc., Franklin, MA (US)

( * ) Notice: Subject to any disclaimer, the term of this patent is extended or adjusted under 35 U.S.C. 154(b) by 907 days.

(21) Appl. No.: 10/600,175

(22) Filed: Jun. 20, 2003

(65) Prior Publication Data

US 2004/0260322 A1 Dec. 23, 2004

(51) Int. Cl.
*A61B 18/18* (2006.01)
(52) U.S. Cl. .......................................... 606/15; 606/7
(58) Field of Classification Search ............... 606/7, 606/10, 14–19; 607/88, 89; 128/898
See application file for complete search history.

(56) References Cited

U.S. PATENT DOCUMENTS

| 467,852 | A | 1/1892 | Buckelew |
|---|---|---|---|
| 1,858,544 | A | 5/1932 | Erickson |
| 2,267,110 | A | 12/1941 | Kinley et al. |
| 3,271,869 | A | 9/1966 | Ratner |
| 3,505,987 | A | 4/1970 | Heilman |
| 3,533,166 | A | 10/1970 | Pine, Jr. |
| 3,555,689 | A | 1/1971 | Cubberly |
| 3,772,794 | A | 11/1973 | Hopler, Jr. |
| 4,213,246 | A | 7/1980 | Stevens |
| 4,407,157 | A | 10/1983 | Lichtenberg |
| 4,411,648 | A | 10/1983 | Davis et al. |
| 4,587,975 | A | 5/1986 | Salo et al. |
| 4,728,123 | A | 3/1988 | Kassal et al. |
| 5,074,871 | A | 12/1991 | Groshong |
| 5,171,248 | A | 12/1992 | Ellis |
| 5,176,693 | A | 1/1993 | Pannek, Jr. |
| 5,238,005 | A | 8/1993 | Imran |
| 5,275,169 | A | 1/1994 | Afromowitz et al. |
| 5,356,382 | A | 10/1994 | Picha et al. |
| 5,366,490 | A | 11/1994 | Edwards et al. |
| 5,370,685 | A * | 12/1994 | Stevens ................ 623/2.11 |
| 5,398,691 | A | 3/1995 | Martin et al. |
| 5,411,552 | A | 5/1995 | Andersen et al. |
| 5,428,903 | A | 7/1995 | Pocci |
| 5,465,732 | A | 11/1995 | Abele |
| 5,470,330 | A * | 11/1995 | Goldenberg et al. ........ 606/7 |
| 5,499,995 | A | 3/1996 | Teirstein |
| 5,545,214 | A * | 8/1996 | Stevens ................ 606/191 |
| 5,554,185 | A | 9/1996 | Block et al. |
| 5,562,665 | A | 10/1996 | Young |
| 5,607,462 | A | 3/1997 | Imran |

(Continued)

OTHER PUBLICATIONS

Boudjemline et al., "Steps Toward Percutaneous Aortic Valve Replacement", Circulation, 2002 American Heart Association, Inc., pp. 775-778, Feb. 12, 2002.

(Continued)

*Primary Examiner*—Ahmed M Farah
(74) *Attorney, Agent, or Firm*—Iandiorio Teska & Coleman

(57) ABSTRACT

An endovascular tissue removal device including a lumen including a rotatable terminal hub advanceable in vasculature, at least one fiber extending from the hub for ablating tissue, and an expandable mechanism connected to the fiber for biasing it into position for precisely ablating tissue as the hub rotates.

6 Claims, 10 Drawing Sheets

U.S. PATENT DOCUMENTS

| | | | | |
|---|---|---|---|---|
| 5,693,043 | A | * | 12/1997 | Kittrell et al. ............. 606/15 |
| 5,725,521 | A | * | 3/1998 | Mueller ..................... 606/7 |
| 5,725,523 | A | * | 3/1998 | Mueller ..................... 606/15 |
| 5,830,210 | A | * | 11/1998 | Rudko et al. ............... 606/15 |
| 5,840,081 | A | | 11/1998 | Andersen et al. |
| 5,885,244 | A | | 3/1999 | Leone et al. |
| 5,899,915 | A | | 5/1999 | Saadat |
| 5,957,916 | A | * | 9/1999 | Jeevanandam et al. ....... 606/15 |
| 6,010,511 | A | | 1/2000 | Murphy |
| 6,023,638 | A | * | 2/2000 | Swanson .................. 600/510 |
| 6,033,359 | A | | 3/2000 | Doi |
| 6,056,743 | A | * | 5/2000 | Ellis et al. .................. 606/15 |
| 6,081,737 | A | | 6/2000 | Shah |
| 6,106,515 | A | * | 8/2000 | Winston et al. ............. 606/15 |
| 6,110,200 | A | | 8/2000 | Hinnenkamp |
| 6,168,614 | B1 | | 1/2001 | Andersen et al. |
| 6,287,321 | B1 | | 9/2001 | Jang |
| 6,423,055 | B1 | | 7/2002 | Farr et al. |
| 6,425,916 | B1 | | 7/2002 | Garrison et al. |
| 6,450,976 | B2 | | 9/2002 | Korotko et al. |
| 6,485,485 | B1 | | 11/2002 | Winston et al. |
| 6,517,515 | B1 | | 2/2003 | Eidenschink |
| 6,560,889 | B1 | | 5/2003 | Lechen |
| 6,616,629 | B1 | * | 9/2003 | Verin et al. ............. 604/101.05 |
| 6,656,204 | B2 | * | 12/2003 | Ambrisco et al. ........... 606/200 |
| 6,764,453 | B2 | | 7/2004 | Meier |
| 6,908,478 | B2 | | 6/2005 | Alferness et al. |
| 2002/0045848 | A1 | | 4/2002 | Jaafar et al. |
| 2002/0058995 | A1 | | 5/2002 | Stevens |
| 2002/0095116 | A1 | | 7/2002 | Strecter |

OTHER PUBLICATIONS

Cardima *Naviport Defectable Tip Guiding* Catheter Brochure, Oct. 2001.
U.S. Appl. No. 10/753,693, filed Jan. 7, 2004, Rudko et al.
U.S. Appl. No. 10/628,794, filed Jul. 28, 2003, Rudko et al.
U.S. Appl. No. 10/447,532, filed May 29, 2003, Rudko et al.

\* cited by examiner

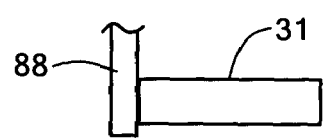
FIG. 10
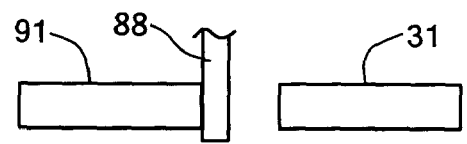
FIG. 11
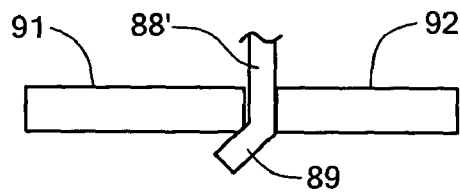
FIG. 12
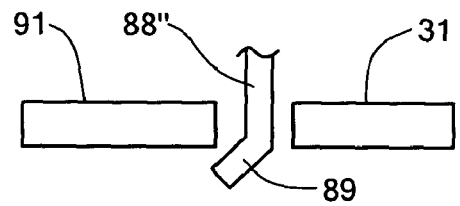
FIG. 13
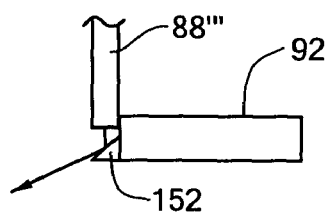
FIG. 14
FIG. 15
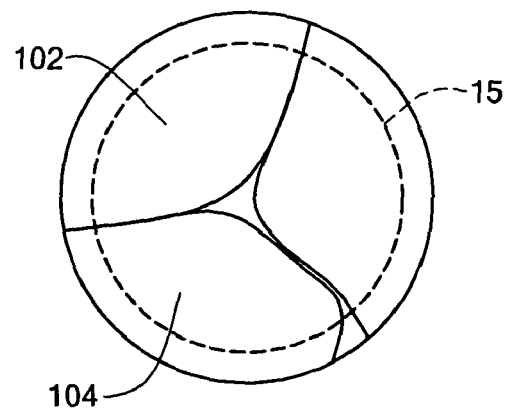

ENDOVASCULAR TISSUE REMOVAL DEVICE

FIELD OF THE INVENTION

This invention relates to endovascular aortic valve replacement.

BACKGROUND OF THE INVENTION

Currently, replacement of a malfunctioning heart valve is accomplished by a major open-heart surgical procedure requiring general anesthesia, full cardio-pulmonary bypass with complete cessation of cardio-pulmonary activity, and a long period of hospitalization and recuperation. In most cases, the native valve is resected (cut-out) and the replacement valve then installed.

As an alternative to open heart surgery, those skilled in the art have attempted to devise systems for endovascular heart valve replacement to overcome the disadvantages associated with open-heart surgery. U.S. Pat. No. 5,370,685, for example, discloses a procedure device capsule connected to a tube and delivered to the site via a guide wire introduced in the femoral artery of a patient. The device capsule houses an expandable barrier attached to balloon segments. Once the guide wire is removed and the barrier is expanded, a tissue cutting blade assembly is advanced in the tube and rotated by a DC motor to resect the existing valve. The barrier traps any debris cut by the tissue cutting blade assembly. Tissue is then suctioned out via the tube. Next, the cutting blade assembly is removed, the barrier balloons are deflated, and the barrier is brought back into the capsule and the capsule itself is removed.

Then, a valve introducer capsule is advanced to the situs. The capsule houses a replacement valve and includes a pusher disk and inflatable balloon segments. After the balloon segments are inflated, the pusher disk pushes the replacement valve into position and a mounting balloon is used to expand the replacement valve and to secure it in place. Then, the introducer capsule is removed. The '685 patent is hereby incorporated herein. See also U.S. Pat. Nos. 5,545,214; 6,168,614; 5,840,081; 5,411,552; 5,370,685; and published patent application No. U.S. 2002/0058995 A1. These patents are also incorporated herein.

The problem with such a system is that the tissue cutting blade assembly is less than optimal and does not provide very precise cutting especially given the fact that the native valve is made of both soft and hard tissue because it is heavily calcified or contains fibrotic tissue. Thus, the blades may buckle or bind as they alternately contact soft and hard tissue.

It is also presumed that pressure must be exerted on the blades. Control of this pressure and the control of the rotation rate, however, is not disclosed in the '685 patent. There is no margin for error in the resection procedure. If too much tissue is cut in certain areas, for example, the aorta can be permanently damaged. Moreover, the native valve typically fails because of calcification of the valve resulting in stenosis or insufficiency. Using cutting blades for valve resection and an improper orientation or improper pressure on the cutting blades or the wrong rate of rotation can result in too little or too much tissue removal and/or imprecise cutting and/or blade buckling or binding as the blades alternately contact soft and hard (calcified) tissue.

Other relevant art includes the following, also included herein by this reference. Published Patent Application No. U.S. 2002/0095116 A1 discloses an aortic filter, an artery filter, and a check valve attached to the distal end of a cannula for resecting an aortic valve from within the aorta. The mechanism for resecting the aortic valve, however, is not disclosed. U.S. Pat. No. 6,287,321 also discloses a percutaneous filtration catheter. U.S. Pat. No. 5,554,185 discloses an inflatable prosthetic cardiovascular valve but does not disclose any specific method of resecting the existing or native valve.

U.S. Pat. No. 6,425,916 discloses a percutaneous approach with a valve displacer for displacing and holding the native valve leaflets open while a replacement valve is expanded inside the native valve. In this way, the native valve does not need to be resected. In many cases, however, such a procedure can not be carried out due to the poor condition of the native valve. And, because the native valve occupies space, the largest aperture possible for the replacement valve may not provide sufficient blood flow.

U.S. Pat. Nos. 6,106,515 and 6,485,485, also incorporated herein by this reference, disclose various expandable laser catheter designs.

BRIEF SUMMARY OF THE INVENTION

It is therefore an object of this invention to provide a more precise tissue cutting apparatus for endovascular heart valve, replacement.

It is a further object of this invention to provide such a tissue cutter which is more effective than prior art blade type tissue cutters.

It is a further object of this invention to provide a tissue cutter which provides effective resection even if the valve is heavily calcified or has fibrotic tissue.

It is a further object of this invention to provide such a tissue cutter which does not require a high rate of rotation.

It is a further object of this invention to provide such a tissue cutter which eliminates the need for precise pressure control.

The invention results from the realization that a more effective and more precise tissue cutting apparatus for endovascular heart valve replacement is effected by a number of optical fibers connected to a mechanism for spreading the fibers into position for resection by laser ablation and also for collapsing the fibers together for vascular insertion and removal.

This invention features an endovascular tissue removal device comprising a lumen (e.g. an optical fiber within a catheter) including a rotatable terminal hub advanceable in vasculature, at least one fiber extending from the hub for ablating tissue, and an expandable mechanism (e.g., a balloon) connected to the fiber for biasing it into position for precisely ablating tissue as the hub rotates. In the preferred embodiment, there are a plurality of fibers extending from the hub and connected to the expandable mechanism so that the plurality of fibers can be spread apart for tissue ablation and also collapsed together for vascular insertion and removal. Typically, the circumferentially expanding balloon is formed in two circumferential rings, one inside and one outside of the distal end of the fiber. The lumen or catheter may include an inflation conduit therein connected to the balloon. The fiber may be an optical fiber or a waveguide.

An endovascular tissue removal device in accordance with this invention features a hub advanceable in vasculature, a plurality of fibers extending from the hub for ablating tissue, and an expandable mechanism (e.g., a balloon) connected to the plurality of fiber for spreading the fibers into position for resection and for collapsing the fibers together for vascular insertion and removal.

This invention also features a method of removing a heart valve, the method comprising introducing a lumen within the vasculature of a patient to a situs proximate a heart valve to be resected, introducing ablative energy into the lumen, and rotating the lumen to resect the heart valve.

In a complete system, a tissue trap device typically surrounds the expandable mechanism. The fiber preferably includes an angled distal portion to ensure only valve tissue is cut. A mirror may also be used for redirecting the ablation energy inward.

An expandable mechanism such as a balloon may be included inflatable on the ventricular side of the valve for supporting the leaflets of the valve. An absorptive surface on the expandable mechanism absorbs ablation energy.

One endovascular tissue removal device in accordance with the invention includes a fiber advanceable within vasculature to ablate tissue, an outer expandable balloon, and an inner expandable balloon spaced from the outer expandable balloon forming a space within which the fiber travels to resect tissue. Typically, the outer expandable balloon is a portion of a tissue trap device, the distal end of the fiber is angled, and an expandable mechanism is inflatable on the ventricular side of the valve for supporting the leaflets of the valve.

BRIEF DESCRIPTION OF THE DRAWINGS

Other objects, features and advantages will occur to those skilled in the art from the following description of a preferred embodiment and the accompanying drawings, in which:

FIG. 10 is a schematic cross-sectional view showing an embodiment of a tissue cutting subsystem in accordance with the subject invention wherein the fiber or fibers are attached to and rotate with the tissue trap subsystem;

FIG. 11 is a schematic cross-sectional view showing another example of the subject invention where the fiber or fibers are rotatable within the tissue trap device;

FIG. 12 is a schematic cross-sectional view showing an embodiment of the tissue cutter of the subject invention wherein the fiber includes an angled distal tip portion;

FIG. 13 is a schematic cross-sectional view showing still another embodiment of the tissue cutter subsystem of the subject invention wherein the fiber rotates between an inner balloon and the outer balloon;

FIG. 14 is a schematic cross-sectional view showing another example of a tissue cutter device. in accordance with the subject invention wherein the fiber is attached to a balloon with a mirror for redirecting the laser energy inward; and FIG. 15 is a schematic top view showing a tissue cutting line possible in accordance with the subject invention.

DISCLOSURE OF THE PREFERRED EMBODIMENT

Figure 1:
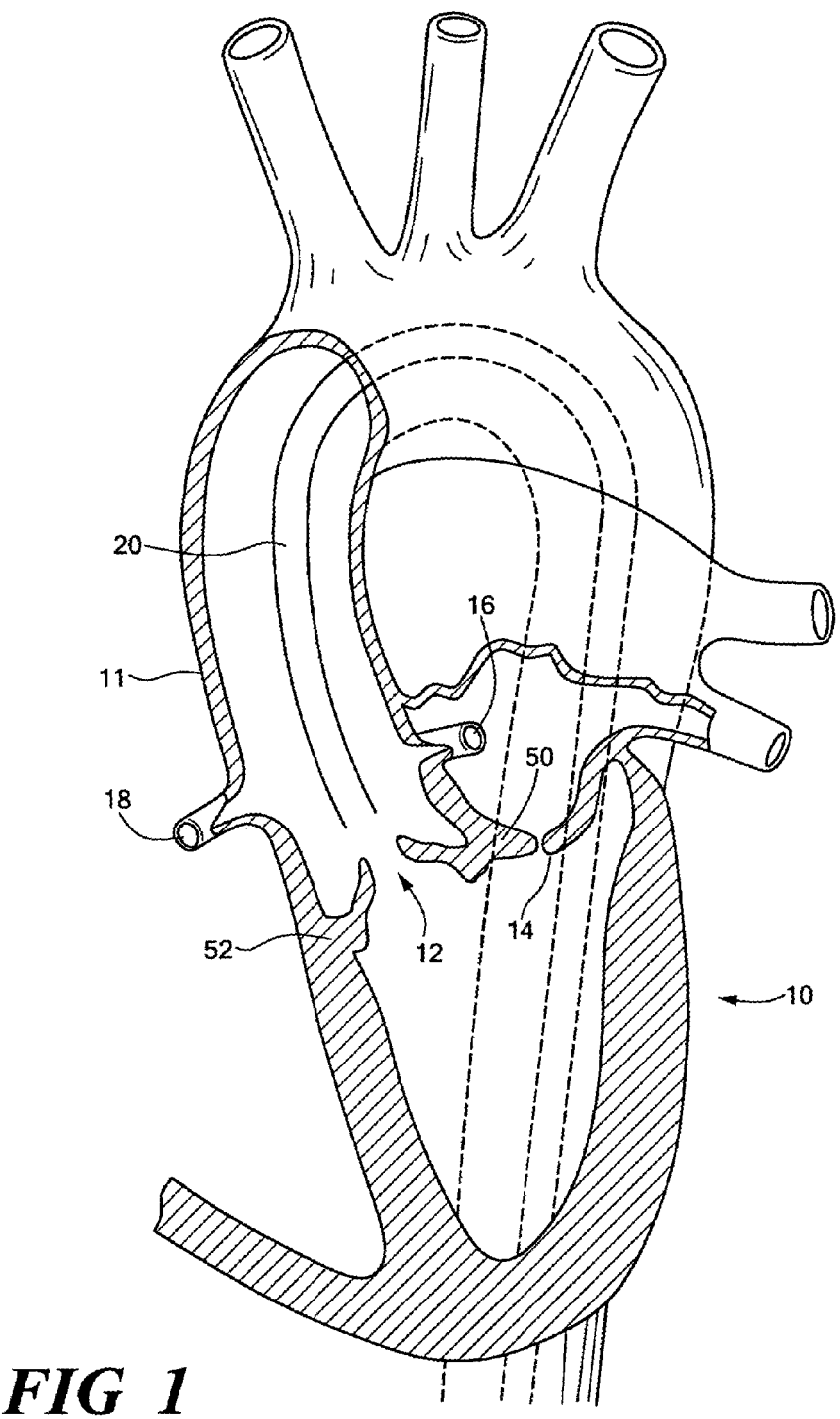
FIG. 1 is a schematic view showing a typical human heart.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings.

Figure 2:
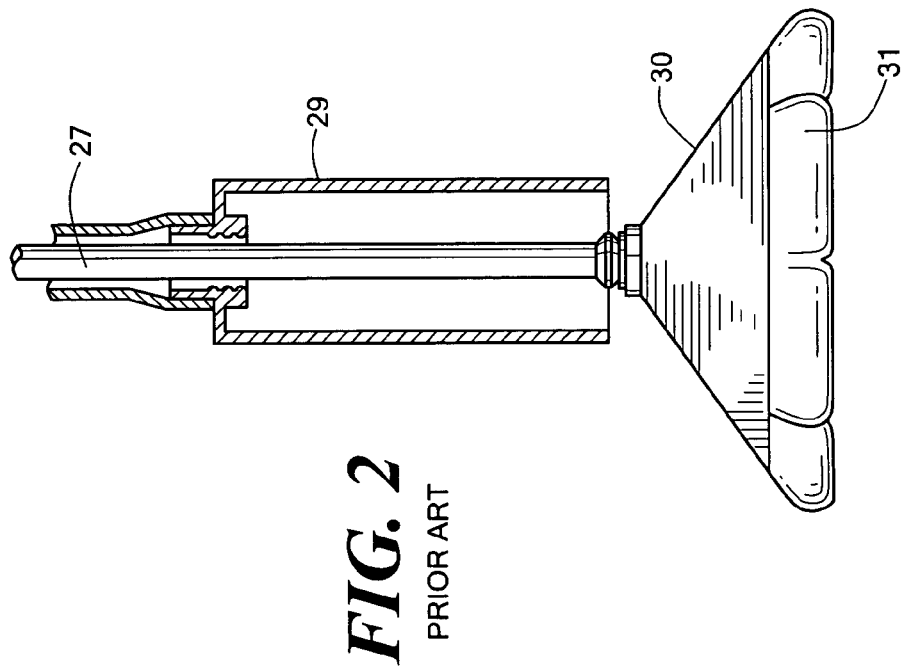
FIG. 2 is a schematic view of a prior art inflatable barrier used in endovascular aortic valve replacement procedures.

FIG. 1 schematically shows heart 10 with aorta 11, aortic valve 12, mitral valve 14, and coronary arteries 16 and 18. The idea behind percutaneous valve replacement surgery is to deliver a catheter 20 proximate valve 12 to resect it and to secure a replacement prosthetic valve in place. Resecting the native valve, however, is problematic. Those skilled in the art have devised inflatable barriers such as barrier 30 with inflatable balloon segments 31, FIG. 2 used to trap tissue during resection. See also U.S. Pat. No. 6,287,321 and Published Patent Application No. U.S. 2002/0095116 A1. Barrier 30 traps any tissue cut during valve resection.

Figure 3:
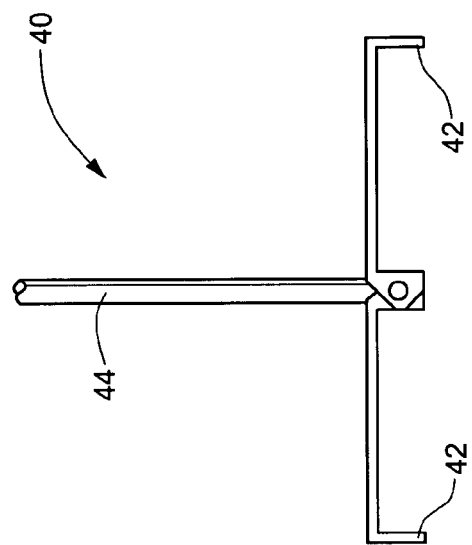
FIG. 3 is a schematic view showing a prior art tissue cutter used in endovascular aortic valve replacement procedures.

But, the only known mechanism for resection of the native valve tissue is tissue cutter 40, FIG. 3 with blades 42. Tissue cutter 40 is connected to shaft 44 rotated by a DC motor presumably at a very high rate of rotation in order to effect tissue cutting. It is also presumed that pressure must be exerted on the blades. Control of this pressure and the control of the rotation rate, however, is not disclosed in the '321 patent.

As shown in FIG. 1, there is no margin for error in the resection procedure. If too much tissue is cut in areas 50 or 52, for example, the aorta can be permanently damaged. Moreover, existing valve 12 (or 14) typically fails because of calcification of the valve resulting in stenosis or insufficiency. Using cutting blades for valve resection and an improper orientation or improper pressure on the cutting blades or the wrong rate of rotation can result in too little or too much tissue removal and/or imprecise cutting and/or blade buckling or binding as the blades alternately contact soft and hard (calcified) tissue.

The problem is so profound that some skilled in the art have attempted to eliminate native valve resection and instead theorize that a prosthetic valve can be expanded directly within native valve 12 (or 14) using a valve displacer to hold the native valve open. Again, however, due to the condition of the native valve, such a procedure is not always possible or effective.

Figure 4:
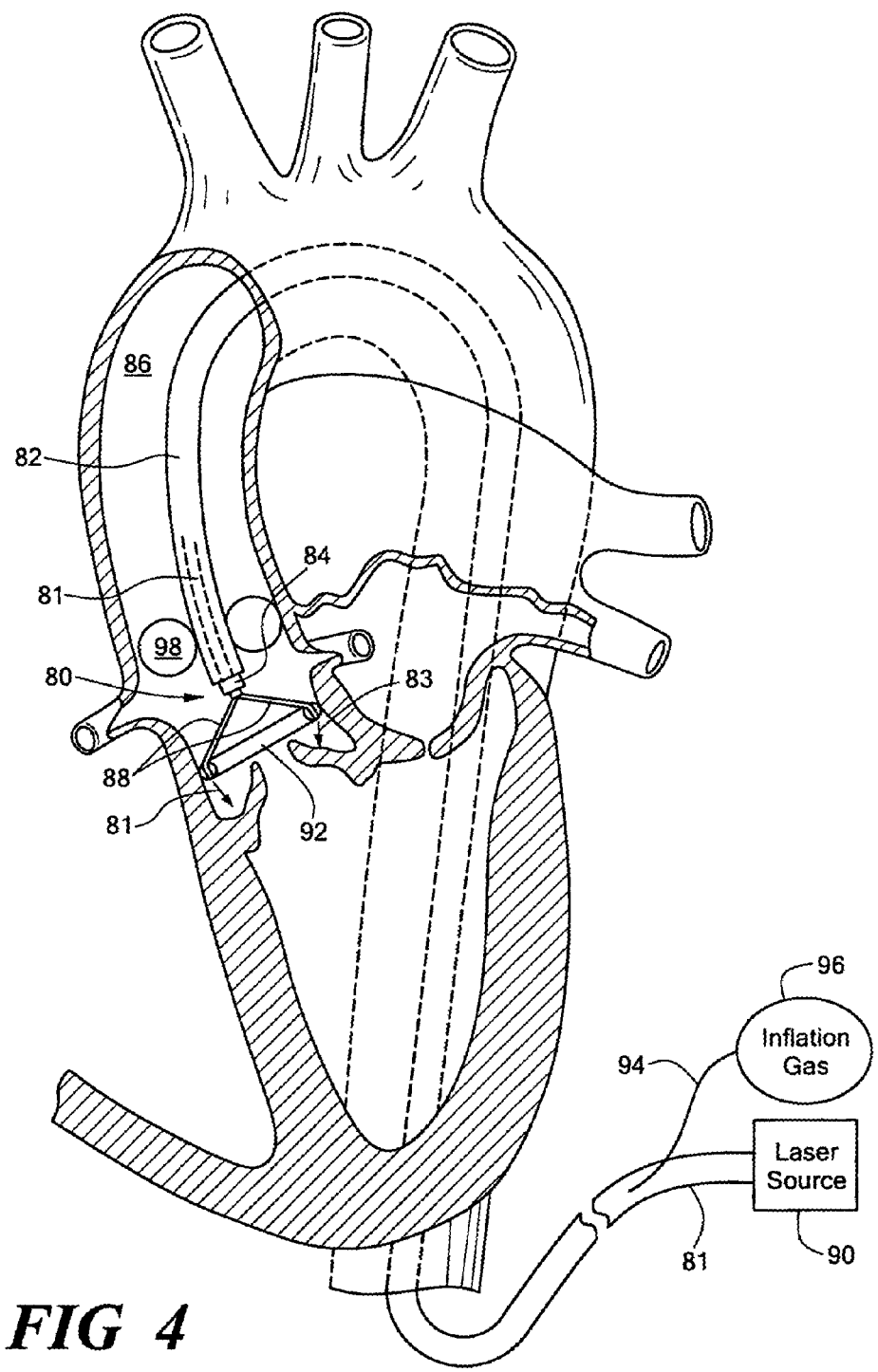
FIG. 4 is a schematic view of a typical human heart depicting the precise nature of the tissue ablation possible with the endovascular tissue removal device of the subject invention.

In accordance with the subject invention, endovascular tissue removal device 80, FIG. 4 includes lumen 82 (e.g. an optical fiber or waveguide or a catheter enclosing an optical fiber or waveguide) with rotatable terminal hub 84 advanced in vasculature 86. At least one but preferably a plurality of fibers 88 (optical fibers or waveguides) extend from hub 84 for ablating tissue—not by blade contact as in the prior art discussed above, but preferably by laser ablation energy. Thus, in the preferred embodiment, optical fiber or waveguide 81 in lumen 82 is connected to laser source 90. Other sources of ablation energy may also be used. Tissue removal device 80 also includes an expandable mechanism connected to the fibers for biasing them into position for precisely ablating tissue as hub 84 is rotated. In the preferred embodiment, the expandable mechanism is circumferentially expanding balloons 91 and 92, FIG. 5 which spread apart the fibers for ablation and which collapse them together for vascular insertion and removal. Inflation conduit 94, FIG. 4 also in lumen 84 along with the optical fiber connects inflation gas source 96 to balloons 91 and 92 and also to optional registration balloon 98 which registers hub 84 in place for rotation. Thus, lumen 82 is typically a multi-lumen catheter.

Figure 5:
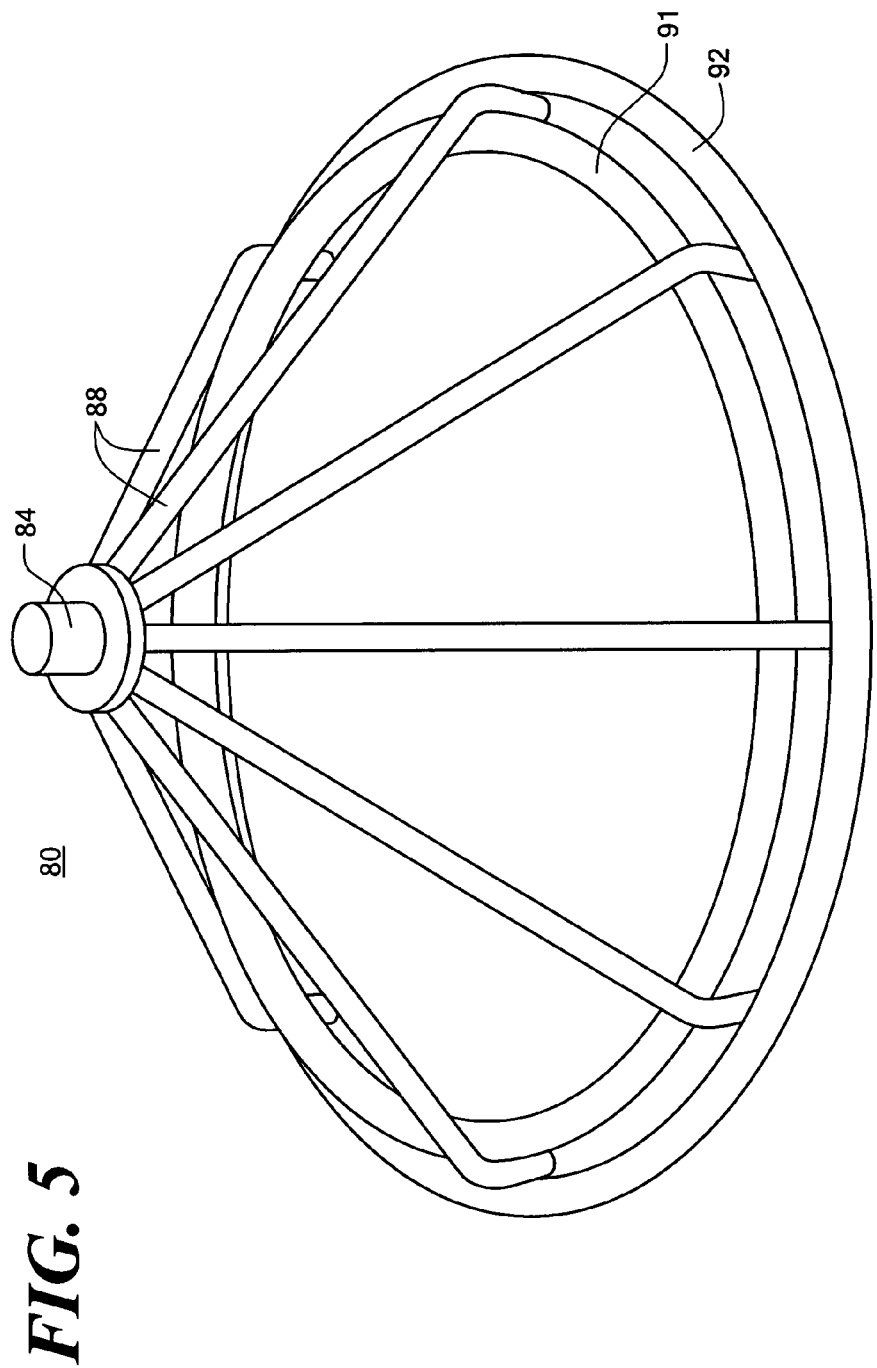
FIG. 5 is a schematic three-dimensional view showing the primary components associated with an endovascular tissue removal device in accordance with the subject invention.
Figure 6:
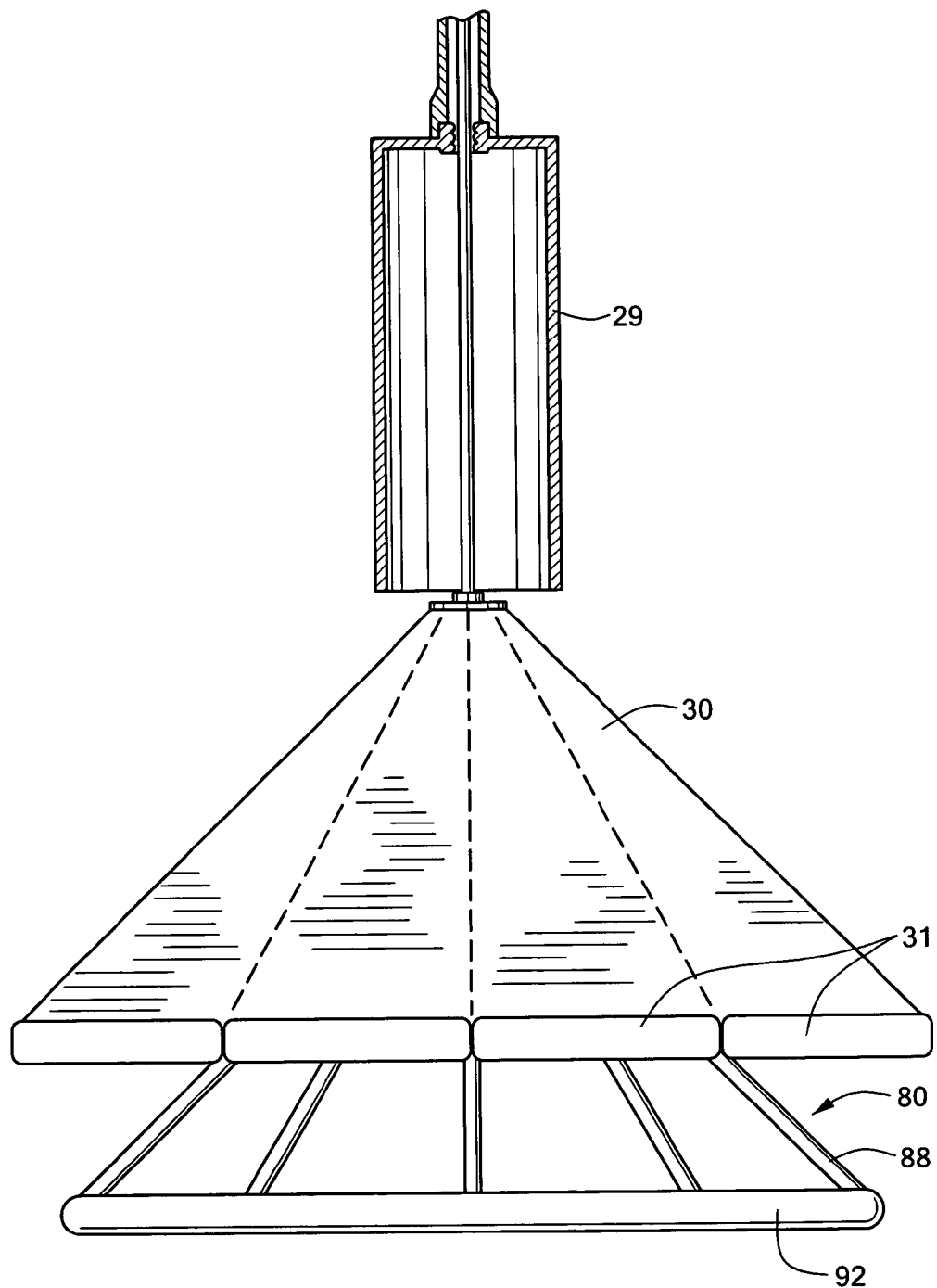
FIG. 6 is a schematic view showing another embodiment of an endovascular tissue removal, device in accordance with the subject invention rotatable within a tissue barrier device.
Figure 7:
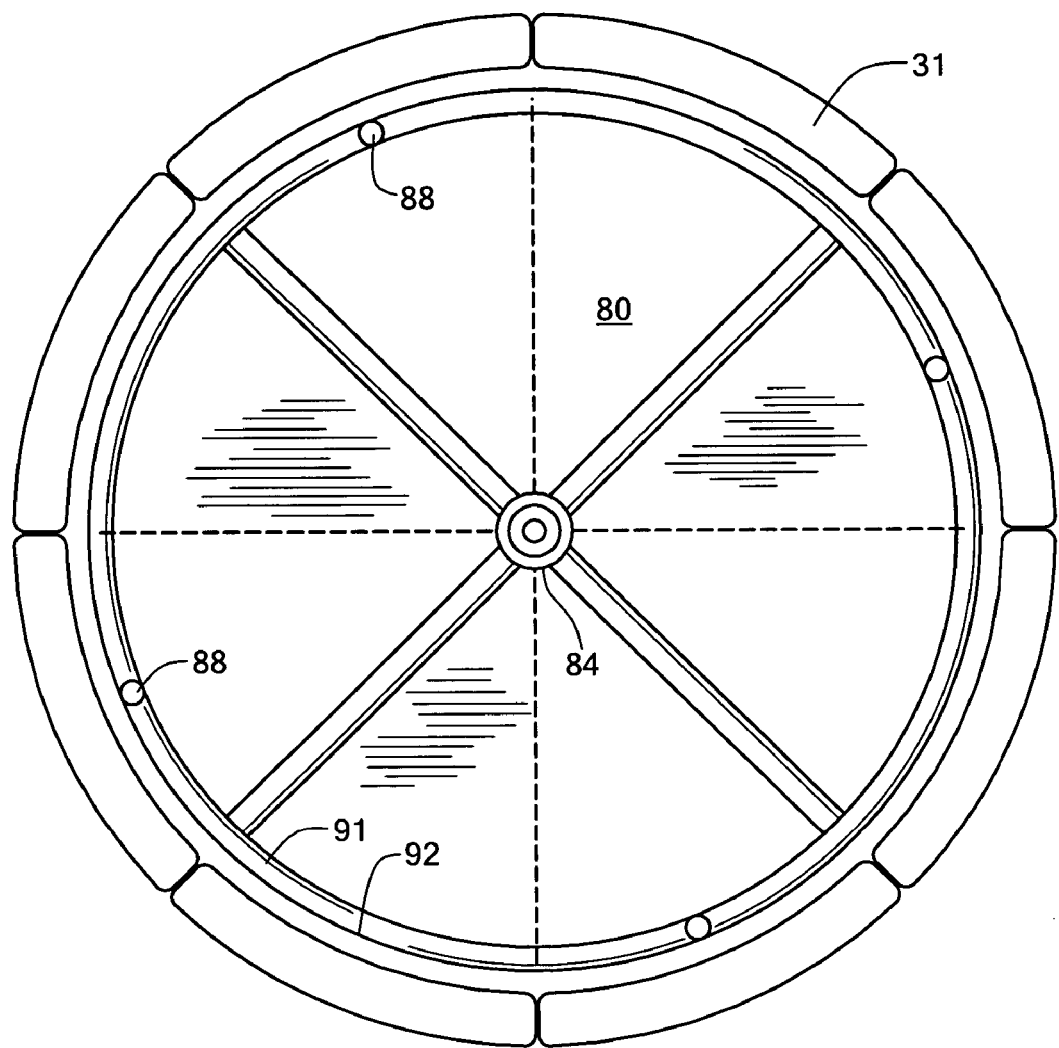
FIG. 7 is a bottom, plan view of the subsystem shown in FIG. 6.

In FIG. 5, spreader balloons 91 and 92 are shown to support the distal end of each optical fiber 88. In FIGS. 6-7 endovascular tissue removal device 80 is used in conjunction with inflatable tissue barrier device 30 and is collapsible within device capsule 29. In one example, the subject invention is used as follows. Device capsule 29 is delivered to the site and balloon segments 31 of barrier 30 expanded. Endovascular tissue removal device 80 still in its collapsed state is then pushed out of device capsule 29 inside of barrier 30 and balloon 92 along with registration balloon 98 (FIG. 4) are inflated. The physician then rotates hub 84 to resect the native valve using laser energy from source 90. After full recession, balloons 91 and 92 are deflated and tissue removal device 80 is brought back within device capsule 29. Tissue is then sucked out of lumen 82 and barrier 30 is brought back into device capsule 29 which is then withdrawn. Finally, a valve introducer is advanced to the site and a replacement valve is installed. Alternately, if there are numerous closely spaced fibers 88, FIG. 5, rotation of the hub may not be required to resect the native valve.

In this way, the problem associated with prior art blade type tissue cutters are eliminated and tissue cutting is more precise by the use of electromagnetic energy in combination with the expandable balloon which spreads apart the plurality of optical fibers 88 and registration balloon 98 which registers the assembly inside the heart for resection typically as hub 84 rotates. The distal ends of optical fibers 88 are preferably precisely oriented to resect only valve tissue as shown by vectors 81 and 83, FIG. 4.

Figure 8A:
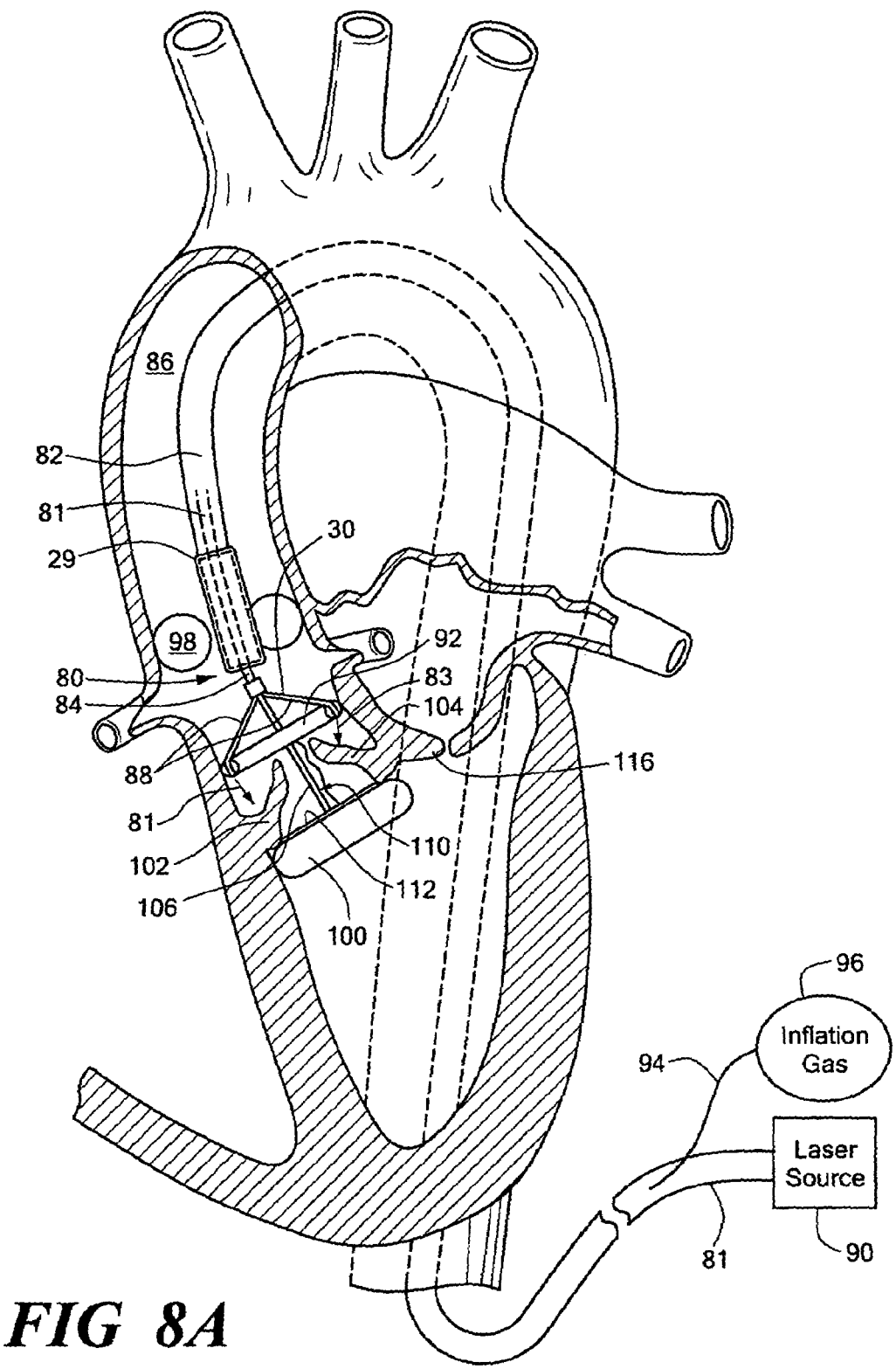
FIGS. 8A-8B are schematic cross-sectional views showing, in one embodiment, a more complete valve resection system in accordance with the subject invention.
Figure 8B:
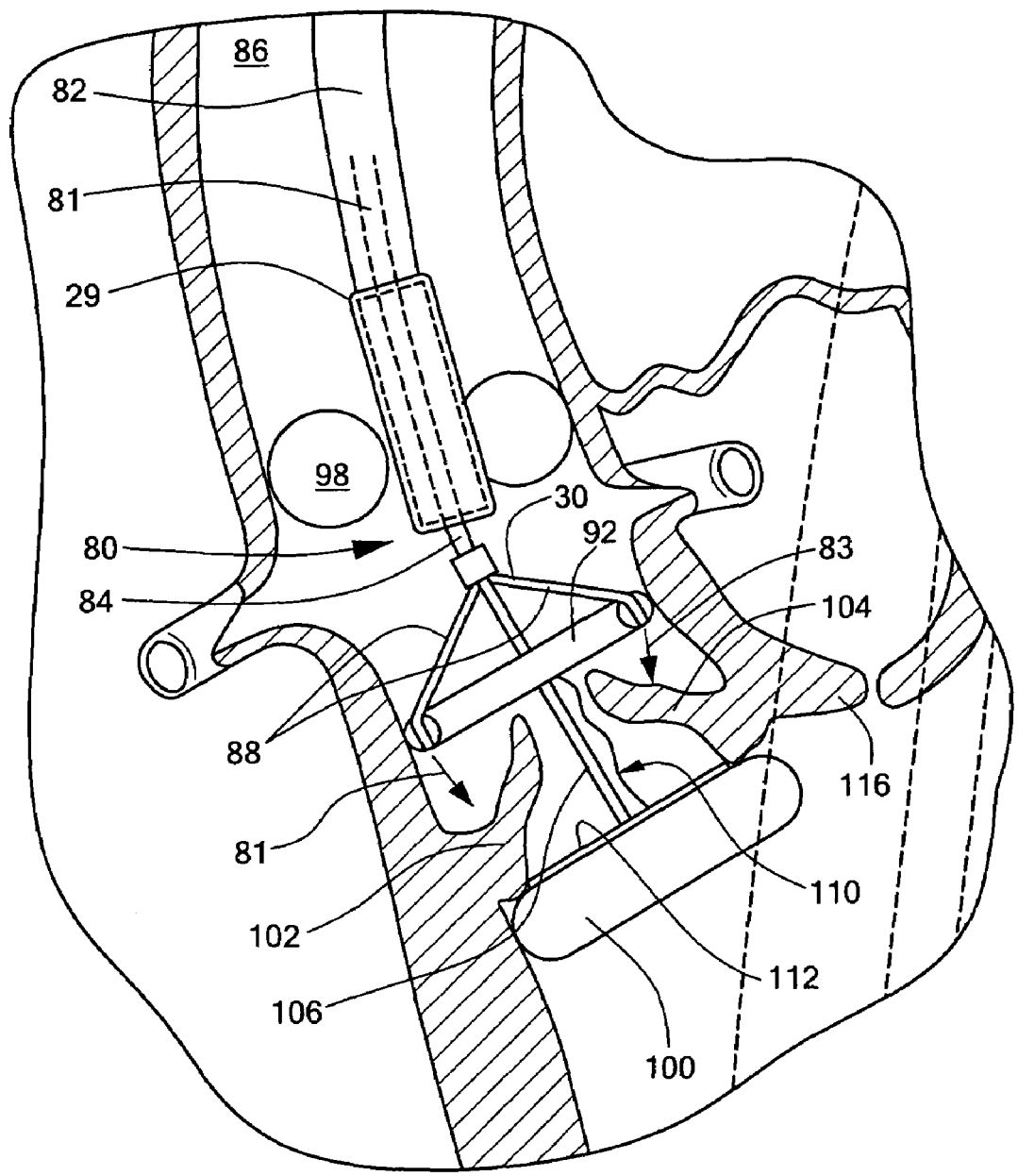
Figure 9:
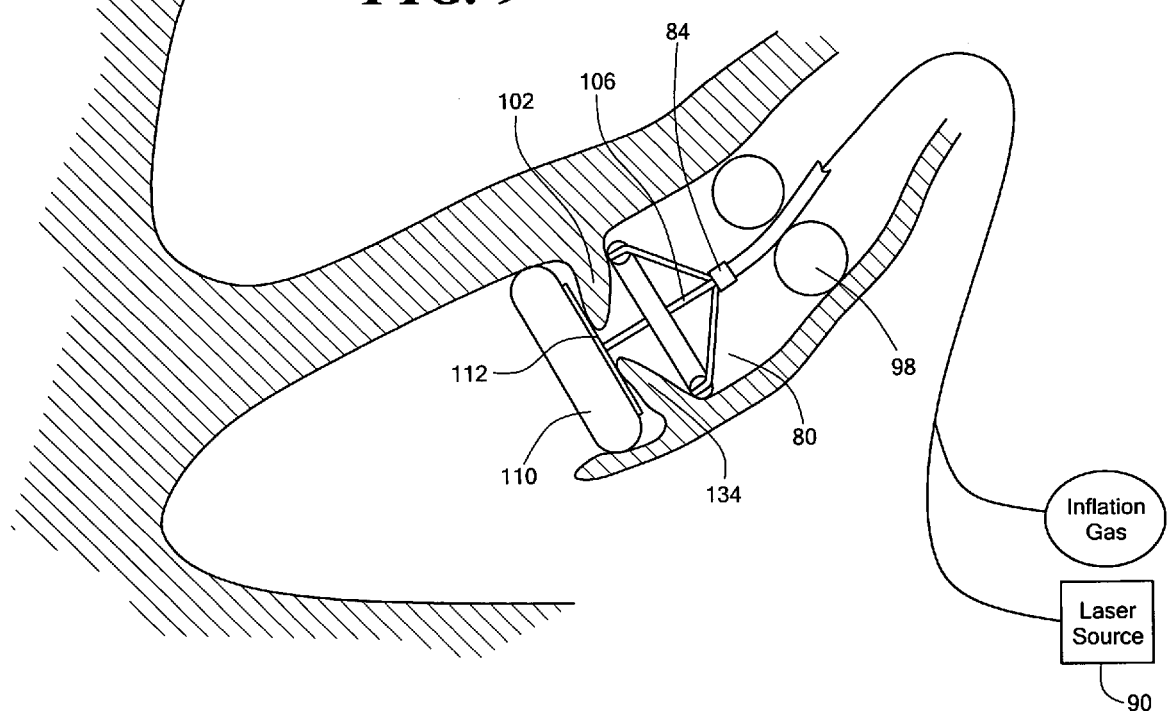
FIG. 9 is another schematic cross-sectional view showing how the lower balloon of the system shown in FIG. 8 supports the valve leaflets.

A more complete system is shown in FIGS. 8A-8B including device capsule 29 (see FIGS. 2 and 6), the tissue removal device (see FIG. 5), and lower balloon 100 disposable on the ventricular side of the heart valve under leaflets 102 and 104. Balloon. 100 is connected to inflation conduit 106 which extends within multi-lumen catheter 81. An outer suction conduit may include port 110 for withdrawing tissue. Balloon 100 performs several important functions. First, it supports leaflets 102 and 104 of the valve as they are pushed closed by tissue removal device 80 as shown in FIG. 9 before cutting for more accurate cutting. Balloon 100 with laser energy absorption layer 112 also prevents inadvertent cutting of any portion of mitral valve 116, FIGS. 8A and 8B.

In still another embodiment, optical fiber 88, FIG. 10 is fixed to balloon 31 of tissue the barrier device and the tissue barrier device is rotated to resect the native valve. In the example of FIG. 11, optical fiber 88 is fixed to single balloon 91 of the tissue cutter and the tissue cutter is rotated within the barrier device to resect the native valve. In the embodiment of FIG. 12, optical fiber 88' is disposed between inner balloon 91 and outer balloon 92 of the tissue cutter device and includes angled distal tip portion 89 to ensure laser energy does not cut areas 50 or 52, FIG. 1. The resulting cut line is shown at 150 in FIG. 15.

In the embodiment of FIG. 13, optical fiber 88" is freely rotatable within the spaces formed between balloon 91 of the tissue removal device and balloon 31 of the tissue barrier device. In this embodiment, it is also preferable that optical fiber 88" includes angled distal tip portion 89.

In the embodiment of FIG. 14, optical fiber 88'" is attached to the inside of balloon 92 of the tissue cutter device which is rotated to resect the native valve. But, the laser energy is directed inward due to mirror 152 on or integral with balloon 92.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

Other embodiments will occur to those skilled in the art and are within the following claims:

What is claimed is:

1. An endovascular tissue removal device comprising:
   a lumen including a rotatable terminal hub advanceable in vasculature;
   at least one fiber extending from the hub for ablating tissue; and
   an expandable mechanism including two balloons, one inside and one outside of the distal end of the fiber connected to the fiber for biasing it into position for precisely ablating tissue as the hub rotates.

2. An endovascular tissue removal device comprising:
   a lumen including a rotatable terminal hub advanceable in vasculature;
   at least one fiber extending from the hub for ablating tissue;
   an expandable mechanism connected to the fiber for biasing it into position for precisely ablating tissue as the hub rotates; and
   a tissue trap device surrounding the expandable mechanism.

3. An endovascular tissue removal device comprising:
   a lumen including a rotatable terminal hub advanceable in vasculature;
   at least one fiber extending from the hub for ablating tissue;
   an expandable mechanism connected to the fiber for biasing it into position for precisely ablating tissue as the hub rotates; and
   a mirror for redirecting the ablation energy.

4. An endovascular tissue removal device comprising:
   a lumen including a rotatable terminal hub advanceable in vasculature;
   at least one fiber extending from the hub for ablating tissue;
   an expandable mechanism connected to the fiber for biasing it into position for precisely ablating tissue as the hub rotates; and
   an expandable mechanism inflatable on the ventricular side of the valve for supporting the leaflets of the valve.

5. The device of claim 4 further including an absorptive surface on the expandable mechanism for absorbing ablation energy.

6. An endovascular valve removal device comprising:
   a lumen including a rotatable terminal hub advanceable in vasculature;
   at least one fiber extending from the hub for ablating valve tissue;
   a first expandable mechanism connected to the fiber for biasing it into position for precisely ablating valve tissue as the hub rotates; and
   a second expandable mechanism inflatable on the ventricular side of the valve for supporting the valve leaflets during resection.

* * * * *